United States Patent [19]
Hustead

[11] Patent Number: 5,134,991
[45] Date of Patent: Aug. 4, 1992

[54] OCULAR PRESSURE-REDUCING DEVICE
[75] Inventor: Robert F. Hustead, Wichita, Kans.
[73] Assignee: Hustead Anesthesiology, P.A., Wichita, Kans.
[21] Appl. No.: 612,993
[22] Filed: Nov. 15, 1990
[51] Int. Cl.$^5$ ............................................. A61F 13/12
[52] U.S. Cl. .................................. 606/204; 606/107; 128/858; 128/25 A
[58] Field of Search ................. 128/25 A, 76 R, 76 S, 128/163, 858, 889; 606/107, 161, 162, 166

[56] References Cited

U.S. PATENT DOCUMENTS

| | | |
|---|---|---|
| 2,209,192 | 7/1940 | Demsey . |
| 2,278,326 | 3/1942 | Leonard . |
| 2,708,928 | 5/1955 | Zienatti ........................ 128/76.5 X |
| 2,818,068 | 12/1957 | De Felice . |
| 3,308,810 | 3/1967 | Galin . |
| 3,952,735 | 4/1976 | Wirtschafter et al. ............. 128/163 |
| 4,167,942 | 9/1979 | Brunelli ............................ 128/254 |
| 4,175,562 | 11/1979 | Honan ........................... 128/163 X |
| 4,193,401 | 3/1980 | Marinello ....................... 128/163 X |
| 4,303,063 | 12/1981 | Stahl ................................ 128/25 A |
| 4,387,707 | 6/1983 | Polikoff ............................ 128/25 A |
| 4,677,974 | 7/1987 | Leonardi ....................... 128/76.5 X |
| 4,727,869 | 3/1988 | Leonardi ............................ 128/163 |
| 4,907,580 | 3/1990 | Leonardi ............................ 128/163 |

FOREIGN PATENT DOCUMENTS

| | | | |
|---|---|---|---|
| 0102805 | 5/1899 | Fed. Rep. of Germany ........ 128/76 |
| 0000038 | of 1876 | United Kingdom ............. 128/25 A |

*Primary Examiner*—Robert Bahr
*Assistant Examiner*—L. Thomas
*Attorney, Agent, or Firm*—Sterne, Kessler, Goldstein & Fox

[57] ABSTRACT

An ocular pressure-reducing device is used to compress the eyelids over the eyeball to help eliminate lymph and/or fluids in the eyelid and orbit, which have been injected or may have accumulated naturally, and which reduces intraocular pressure without primary pressure on the cornea. The device is a hollow bulb which is attached to an elastic band or other mechanism for accommodating placement around a patient's head. An indentation in the base of the bulb has a radius and a curvature such that the indentation fits over the cornea thereby preventing excessive pressure on the cornea. The bulb has a given wall strength which allows it to invaginate between 10 mmHg and 60 mmHg over a narrow range of pressure, thereby further preventing an excessive pressure application on the eye. The invaginated bulb presses against the lids and orbital structures to facilitate removal of fluids in these structures.

6 Claims, 5 Drawing Sheets

OCULAR PRESSURE-REDUCING DEVICE

BACKGROUND OF THE INVENTION

1. Field of the Invention

This invention relates to an ocular pressure-reducing device employed in reducing lymph and/or fluids in the eyelid and orbit, which may have accumulated naturally or were injected during an anesthetic procedure.

2. Description of the Related Art

The eye is essentially a large sphere with a part of a smaller sphere incorporated in the anterior surface, constituting a structure with two radii of curvature (as shown in FIG. 1).

The orbit, which contains the eye, is a bony cavity in the skull housing the eyeball and its associated structures. Such an arrangement creates a cavity capable of containing fluids in or around the eye; this cavity is subdivided by the non-homogeneous structures therein. For example, one such cavity, known as the choroidal space, separates two of the three layers of the eyeball. This space, separating the sclera from the retina (as shown in FIG. 1), may, for example, become filled with blood or other fluids during a surgical procedure. Accumulation of excess fluid in this space can cause traction on the capillaries in the space to cause a sudden increase in intraocular pressure, which precludes further surgery in the eye and possible expulsive hemorrhage with damage to the retina and permanent visual loss. Most eye surgeons like to have the volume of the choroidal space reduced to minimum before "opening the eyeball" for cataract and other forms of eye surgery.

The eyeball is filled with fluids, namely, the aqueous fluid and the vitreous gel. The orbit is filled with muscles and fat, which contain fluids. The amount of this fluid varies considerably from orbit to orbit. The volume of fluid in the orbit is suddenly increased when local anesthetic solutions are injected into the fatty tissues around and behind the eyeball.

Before starting intraocular surgery, most surgeons would like to have a "soft eye" and minimal fluids pressure against the eyeball, as well as a low choroidal and vitreous volume.

Intraocular pressure-reducing devices are commonly used before eye surgery to reduce normal fluids in the eyeball and orbit, any excess fluids which are present in some persons, and fluids injected with anesthetic solutions.

Essentially, devices have been used to exert a pressure on the eyeball such that some of the fluid in the eye are forcibly ejected into the veins which drain the eye. Furthermore, these devices prevent further fluid accumulation by reducing arterial capillary blood flow. Previous devices of this type have utilized articles such as a container of mercury, rubber balls, inflatable balloons and sponges attached to an adjustable headband to apply pressure to the eye. Each of these devices have disadvantages, however. The mercury bag, for example, requires the patient to be immobile and be in the supine position for a predictable application of force.

Furthermore, these devices often lose their effectiveness as fluids exit the orbit thereby decreasing the amount of pressure exerted by the device on the arterial capillaries, allowing fluid to reaccumulate.

In addition, these articles may potentially inflict damage to the eye by directly applying pressure to the cornea and by applying an excessive pressure to the eye so to interfere with the metabolism of the retina and optic nerve. For example, U.S. Pat. No. 4,175,562 to Honan discloses a cup-shaped bellow which bears against the closed eyelid of a patient. The bellow is inflated to apply varying amounts of pressure on the eye. However, one of ordinary skill in the art will appreciate that such a device, in applying pressure directly to the cornea, has the potential for damaging the cornea. Furthermore, the use of this device does not assure a uniform and constant pressure distribution to the eye particularly after fluids have exited the eye thereby decreasing the applied pressure by the bellows on the eye. In spite of the adjustable pressure mechanism connected to the bellow, therefore, pressure application declines with fluid loss. Furthermore the device does not apply uniform pressure to the orbit; for example, it may produce no force on the orbital tissue of large orbits.

U.S. Pat. No. 4,303,063 to Stahl discloses an ocular massage device with an inflatable member placed between a rigid curved plate and a patient's eye. However, such a device shares similar disadvantages with the bellows disclosed above.

Other devices have alleviated some of the above-noted disadvantages while raising new difficulties. U.S. Pat. No. 3,952,735 to Wirshafter et al. appears to disclose an eye bandage for attachment to the area surrounding the eyelid of a patient with a pneumatic cushion composed of a closed cell or multi-cells which may be contoured to provide a desired pressure distribution on the eye of a patient. However, one of ordinary skill in the art will appreciate that such an eye bandage has the potential for creating corneal damage if an excessive pressure is applied to the eye by tightening the eye strap. Furthermore, fluid loss from the orbit will alter the amount of pressure exerted by the device on the eye, thereby hindering a uniform pressure application.

Another ocular pressure-reducing device, named the "Super Pinky," has also been used to reduce intraocular pressure. This device is essentially a hard rubber ball which is applied to the eye to reduce intraocular pressure; it also causes orbital fluid loss. However, such a device also applies potentially damaging pressure directly to the cornea while also potentially damaging the eye. The eye may be particularly damaged if the headstrap which applies the ball to the eye is excessively tightened or, if the eyeball is unable to retreat deep enough into the orbit. Furthermore, as the orbital fluid is resorbed, the device may come to rest on the bony orbit to cause pressure damage or allow fluids to reaccumulate in the eyeball.

SUMMARY OF THE INVENTION

It is an object of the instant invention to safely reduce the orbital and intraocular pressure of a patient by effecting orbital fluid loss upon exerting an external pressure on the eyelids, without direct pressure on the cornea, and which will apply pressure to the orbital content of orbits of large and small volume, whether the eye is forward or deep in the orbital cavity.

It is a further objective of the instant invention to apply a fairly constant and continual pressure to the eye as orbital fluid is resorbed.

It is a further objection of this invention to minimize corneal damage while reducing the ocular pressure of a patient by minimizing any direct pressure application to the cornea of the eye.

It is a further objective of the instant invention to eliminate the potential for damaging the eye as a whole during a reduction of ocular pressure by limiting the maximum amount of external pressure which can be applied to the eye.

The ocular pressure-reducing device of the instant invention alleviates the aforementioned problems associated with the related art through two structurally integral safety features. First, an indentation in the device contours to the shape of the eye to prevent an excessive direct pressure application to the cornea of the eye thereby minimizing corneal damage. Secondly, the device utilized is a hollow bulb which invaginates over a narrow range of pressures thereby preventing the danger of an excessive pressure application to the eye or orbit as a whole.

For a better understanding of the present invention, together with other objects, references are made to the following description, taken in conjunction with the accompanying drawings. The scope of the present invention will be pointed out in the claims.

DETAILED DESCRIPTION OF A PREFERRED EMBODIMENT

Figure 1:
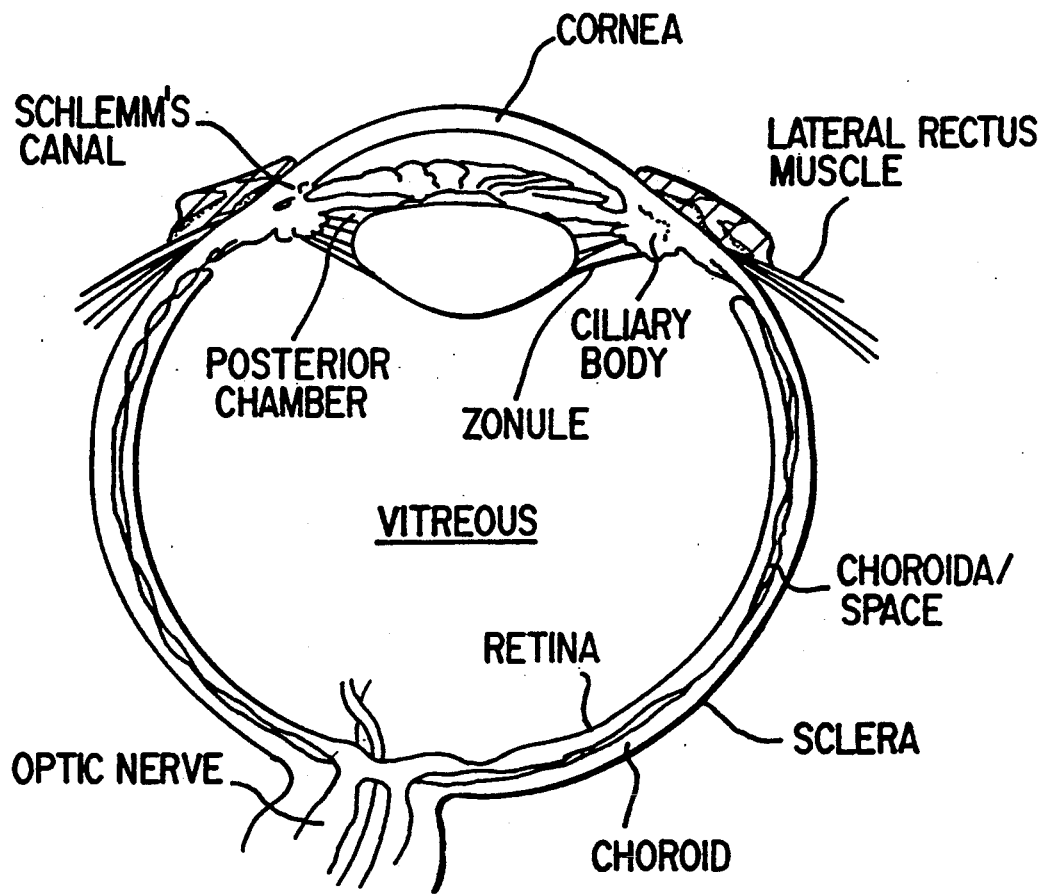
FIG. 1 is a sectional anatomical view of the eye.
Figure 2:
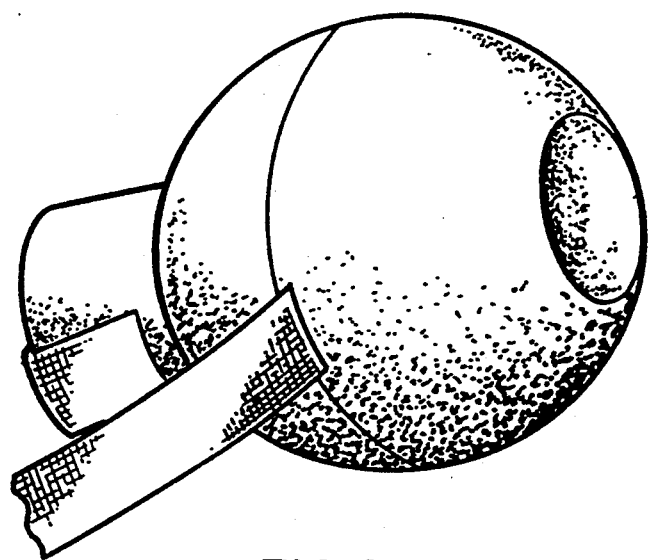
FIG. 2 is a perspective view of a preferred embodiment of the instant invention.
Figure 3:
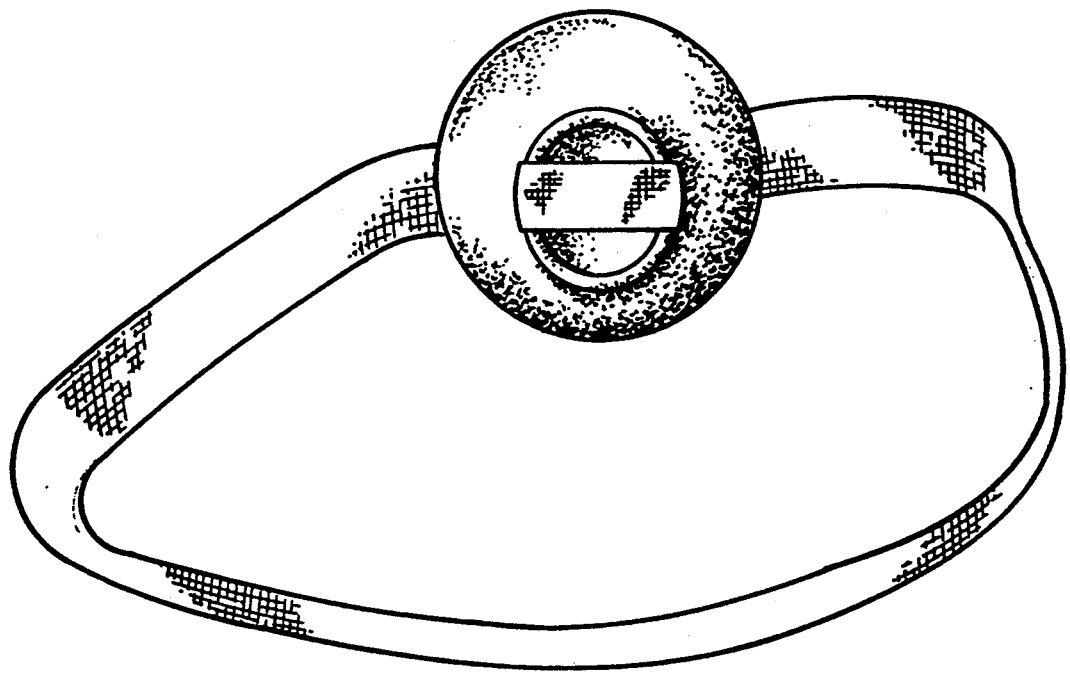
FIG. 3 is a rear view of a preferred embodiment of the instant invention.
Figure 4A:
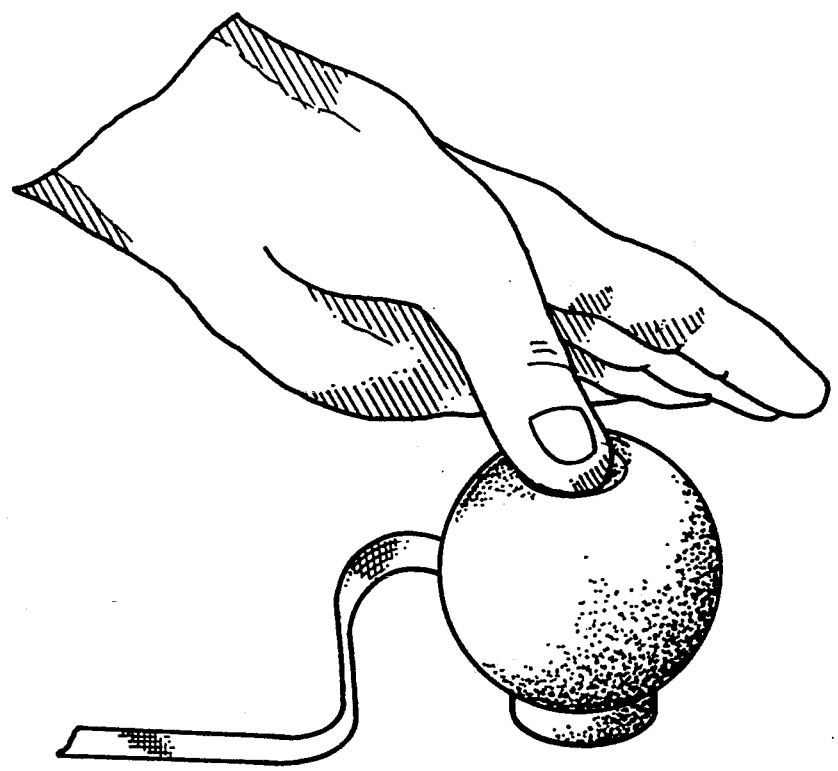
FIG. 4a is a perspective view of a preferred embodiment of the instant invention prior to pressure application.
Figure 4B:
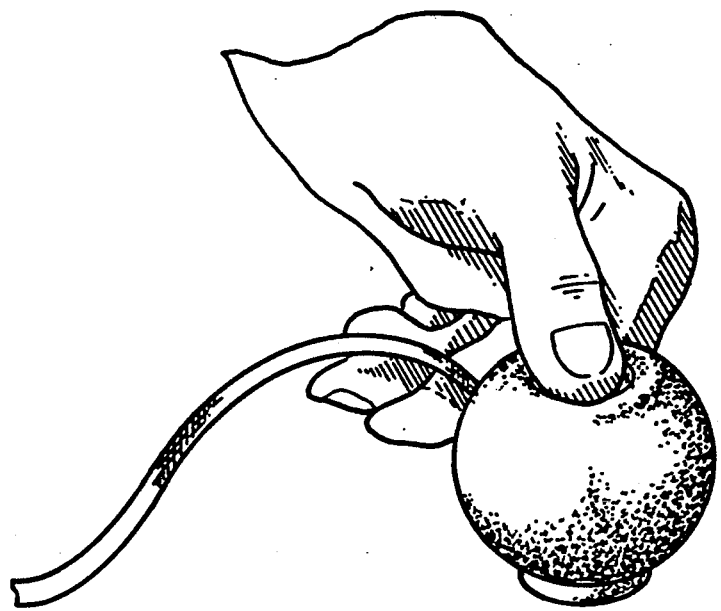
FIG. 4b is a perspective view of a preferred embodiment of the instant invention during a normal pressure application.
Figure 4C:
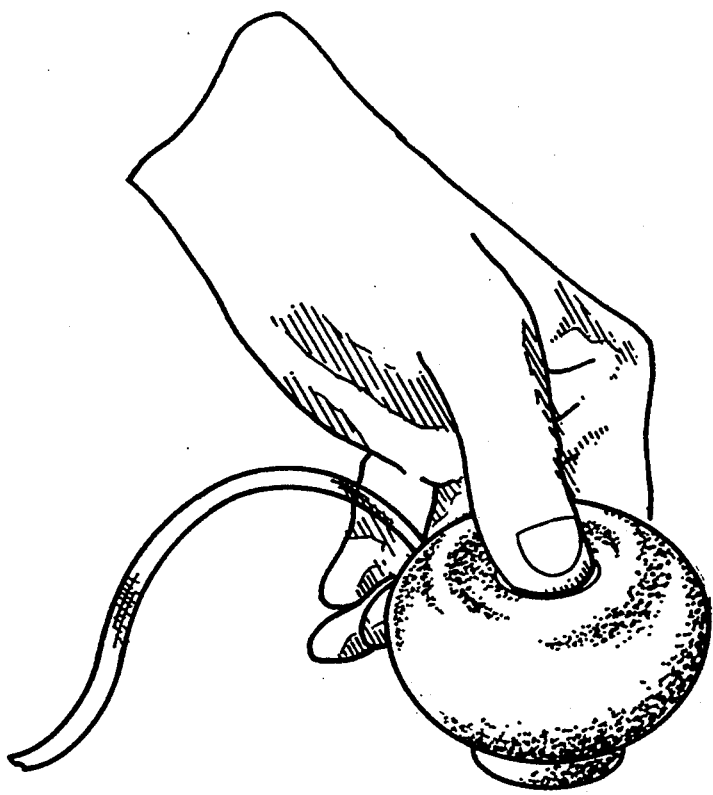
FIG. 4c is a perspective view of a preferred embodiment of the instant invention as it invaginates during an excessive pressure application.

With continuing reference to the drawings, the present invention may take the form of the combination of a hollow bulb 1 with a suitable concavity and an adjustable band 2 used as an ocular pressure-reducing device is shown in FIGS. 2 and 3. As shown in FIGS. 4a, 4b and 4c, the bulb 1 has a given wall strength during manufacture which allows the bulb to invaginate at a clearly defined and narrow range of pressure above 10 mmHg and below 60 mmHg depending on the wall thickness; the physiologic advantages of the use of a 20-35 mmHg pressure application to the eye are evident to those knowledgeable of capillary circulation.

The bulb 1 is preferably made of a resilient plastic material, although other materials with similar strengths and structural characteristics may also be employed. Slits 3a may be cut into the hollow bulb at opposite sides in the equator to permit attachment of strap 2 to bulb 1 and the exit slits 3b in the neck allow for exit of the strap and for adjustment of size and drag. This adjustability makes the device useful to those with different orbital volumes and head sizes. The slits 3b are preferably 7/16 inch in length and the strap 2 is preferably a ⅛ inch thick elastic band that can stretch to approximately 36 inches in length. Naturally, other band attachment means may be employed to practice the invention.

In one embodiment of the invention, the bulb 1 is derived from a standard bulb from an irrigating syringe. The particular bulb may be a modified 60 cc bulb syringe which is approximately 2.375 inches in diameter. (The bulb is manufactured by Premium Plastics of Chicago, Ill.) The use of this bulb in the present invention, however, clearly has little to do with its previous use as an irrigating syringe; the bulb is modified in the present invention so as to accommodate the strap for placement around a patient's head.

Figure 5A:
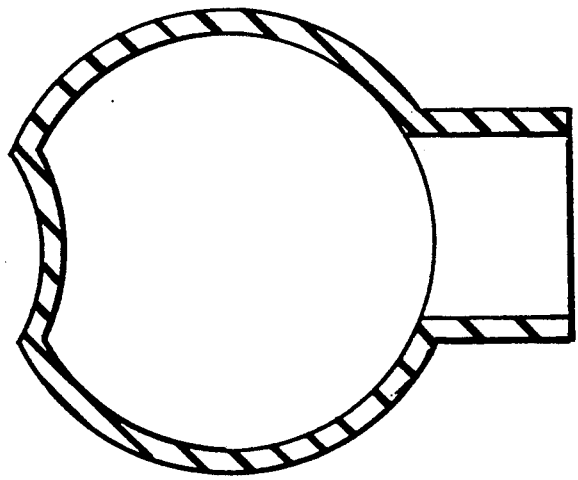
FIG. 5a is a cross-sectional view of a preferred embodiment of the instant invention as applied on the eye.
Figure 5B:
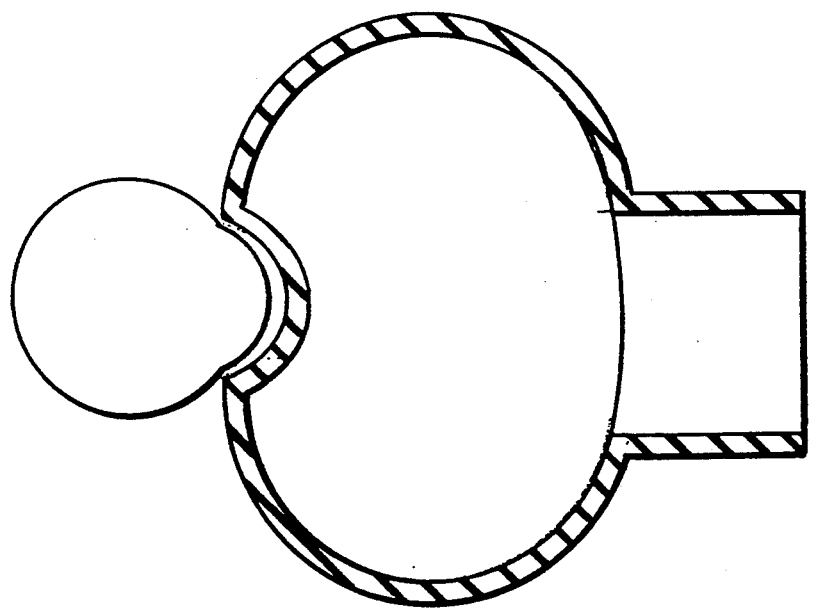
FIG. 5b is a cross-sectional view of a preferred embodiment of the instant invention as it applies pressure on the eye.

Bulb 1, while generally an elongated sphere in shape, has an indentation 4 which conforms to the shape of a patient's eye, particularly to the shape of the patient's cornea. Indentation 4 is generally a surface substantially in the form of a portion of a sphere although similar surfaces will also conform to the shape of a patient's eye. The wall strength of the bulb 1 and the shape of the indentation 4 assure a constant pressure application about the orbit of the eye even after orbital fluid loss is effected. Furthermore, as shown in FIGS. 5a and 5b, the curvature of indentation 4 within the bulb 1 assures that primary contact with the eye is achieved with the sclera, instead of with the cornea.

Figure 6:
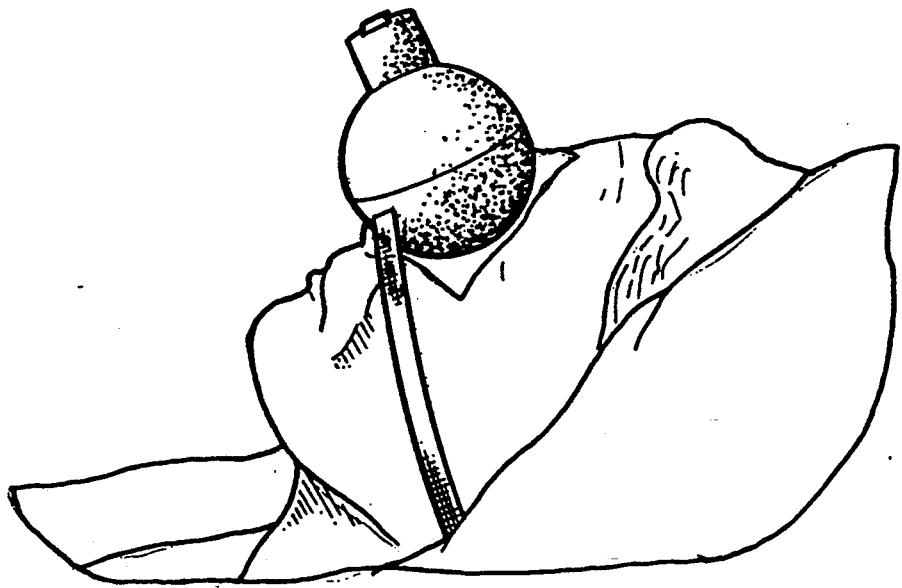
FIG. 6 is a side view of a preferred embodiment of the instant invention as applied to the eye of a patient.

To facilitate the pressure application by the bulb on the eye of a patient, elastic strap 2 is placed around a patient's head as shown in FIG. 6, thereby placing bulb 1 against the patient's orbit. The eyelids of the patient are first closed and held closed by gauze or tape placed over the closed eyelid. Bulb 1 is then applied to the tape or the gauze. The pressure applied by bulb 1 is adjustable by tightening band 2 which is secured about the patient's head. The adjustable band 2 permits the application of varying amounts of pressure about the orbit and facilitates placement of the ocular device around different sized heads.

The amount of pressure applied to the eye, however, is limited by the intrinsic wall characteristics of the bulb 1 itself. If the elastic strap 2 is excessively tightened, the bulb 1 will invaginate as shown in FIG. 4c, thereby preventing an excessive pressure application to the eye. The bulb 1 can be manufactured so as to initially begin to invaginate at a pressure between 10 mmHg and 60 mmHg. Once the bulb begins to invaginate, complete invagination occurs within a narrow range of pressure.

As can be seen, the present invention provides a convenient and safe intraocular pressure-reducing device. Having described the preferred embodiment of the invention in detail, those skilled in the art will appreciate that numerous modifications may be made to the device of the invention without departing from the spirit and scope thereof. Accordingly, the foregoing detailed description of this embodiment should not be considered limiting, and the invention should be limited solely in light of the following claims.

I claim:

1. A device for reducing ocular fluids and pressure comprising:
   (a) a bulb which conforms to the shape of a patient's eye said indentation having a surface substantially in the form of a portion of a sphere, so as to avoid corneal pressure, said bulb being hollow and said bulb defining an indentation which conforms substantially to the shape of the patient's eye and
   (b) means for securing said bulb against the patient's eye.

2. The device of claim 1 wherein the means for securing said bulb against the patient's eye is a band for placing around the patient's head.

3. The device of claim 1 wherein the bulb invaginates at a clearly defined and narrow range of pressure, wherein said range is above 10 mmHg and below 60 mmHg.

4. The device of claim 2 wherein said hollow bulb defines slits for attaching said band to said bulb.

5. An ocular pressure-reducing device comprising:

(a) a hollow bulb which invaginates at a pressure between 10 and 60 mmHg wherein said bulb has an indentation which conforms to the shape of a patient's eye, said indentation having a surface substantially in the form of a portion of a sphere, and (b) strap means for accommodating and tightening said bulb about a patient's head.

6. The ocular pressure-reducing device of claim 5 wherein said bulb invaginates during a narrow range.

* * * * *

UNITED STATES PATENT AND TRADEMARK OFFICE
CERTIFICATE OF CORRECTION

PATENT NO. : 5,134,991
DATED : August 4, 1992
INVENTOR(S) : Robert F. Hustead

It is certified that error appears in the above-indentified patent and that said Letters Patent is hereby corrected as shown below:

Column 2, line 63, delete "objection" and substitute --objective-- therefor;

Column 4, lines 62 and 63, delete "said indentation having a surface substantially in the form of a portion of a sphere,";

Column 4, line 66, after "eye" insert --said indentation having a surface substantially in the form of a portion of a sphere,--.

Signed and Sealed this

Fourteenth Day of September, 1993

Attest:

BRUCE LEHMAN

*Attesting Officer*    *Commissioner of Patents and Trademarks*